United States Patent [19]

Gillis

[11] 4,404,280

[45] Sep. 13, 1983

[54] PROCESS FOR PREPARING MURINE INTERLEUKIN 2 IN THE PRESENCE OF INTERLEUKIN 1 FROM AN INTERLEUKIN 2 NONPRODUCER MALIGNANT CELL LINE AND CELL LINE THEREFOR

[76] Inventor: Steven Gillis, 15509 NE. 198th, Woodinville, Wash. 98072

[21] Appl. No.: 283,092

[22] Filed: Jul. 16, 1981

[51] Int. Cl.³ .................... C12P 21/00; C12N 5/00; C12N 5/02; C12N 1/00; A61K 37/00; C12R 1/91; C12P 1/00

[52] U.S. Cl. .................... 435/68; 435/240; 435/241; 435/317; 424/177; 435/948; 435/41

[58] Field of Search .............. 424/177; 435/68, 317, 435/240, 241, 70, 41

[56] References Cited

PUBLICATIONS

Larsson et al., "Two Distinct Factors are Required for Induction of T-Cell Growth", 283 *Nature* 664–666 (1980).

Gillis et al., "Long Term Culture of Tumor-Specific Cytotoxic T Cells", 268 *Nature* 154 (1977).

Watson et al., "Biochemical and Biological Characterization of Lymphocyte Regulatory Molecules–I. Purification of a Class of Murine Lymphokines", 150 *The Journal of Experimental Medicine* 849 (1979).

Gillis et al., "Biochemical Characterization of Lymphocyte Regulatory Molecules—II. Purification of a Class of Rat and Human Lymphokines", 124 *The Journal of Immunology*, 1954 (1980).

Gillis et al., "Biochemical and Biologic Characterizations of Lymphocyte Regulatory Molecules III, The Isolation and Phenotypic Characterization of Interleukin-2 Producing T Cell Lymphomas", 125 *The Journal of Immunology*, 2570 (1980).

Smith et al., "Functional and Molecular Characteristics of T-Cell Growth Factor", 17 *Molecular Immunology*, 579 (1980).

Farrar et al., "Macrophage-Independent Activation of Helper T Cells I, Production of Interleukin 2", 125 *The Journal of Immunology*, 793 (1980).

Smith et al., "The Functional Relationship of the Interleukins", 151 *The Journal of Experimental Medicine*, 1551–1556 (1980).

Gillis et al.; Proc. Natl. Acad. Sci., USA 78, 1133 (1981).

Smith et al.; Nature 287, 853 (1980).

Farrar et al.; Fed. Proc. 39, 802 (1980).

Oppenheim et al.; Fed. Proc. 40, 1110 (1981).

Shimizu et al.; J. Exp. Med. 152, 1436 (1980).

Gillis et al.; J. Exp. Med. 152, 1709 (1980).

*Primary Examiner*—Alvin E. Tanenholtz
*Assistant Examiner*—James Martinell
*Attorney, Agent, or Firm*—Christensen, O'Connor, Johnson & Kindness

[57] ABSTRACT

A process for producing murine IL-2 from malignant neoplastic cells which are incapable of IL-2 production by mitogen stimulation alone includes culturing murine leukemia or lymphoma cells in vitro in a protein-containing medium supplemented with various additives. A T cell mitogen and IL-1 are added to the culture medium as co-stimulants inducing the production of a supernate which contains IL-2. After a period of time, the supernate is collected and then assayed for IL-2 activity. Also in the present invention, IL-1 is utilized as a co-stimulant together with a suboptimum concentration of a T cell mitogen to induce IL-2 production in cell lines capable of generating IL-2 by mitogen stimulation alone. The use of IL-1 in these instances reduces the quantity of mitogen required to produce maximum levels of IL-2.

13 Claims, 1 Drawing Figure

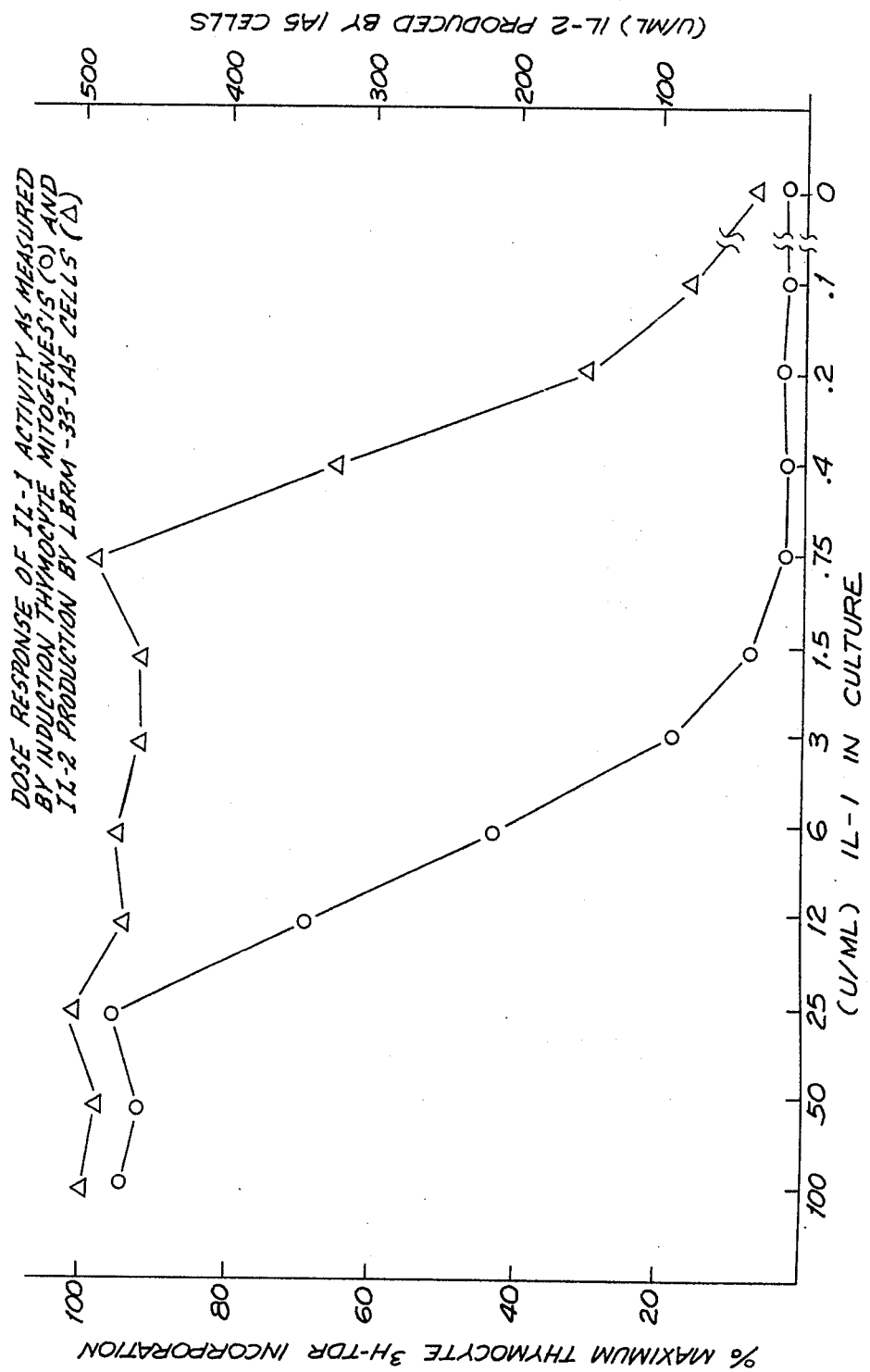

PROCESS FOR PREPARING MURINE INTERLEUKIN 2 IN THE PRESENCE OF INTERLEUKIN 1 FROM AN INTERLEUKIN 2 NONPRODUCER MALIGNANT CELL LINE AND CELL LINE THEREFOR

DESCRIPTION

Technical Field

The present invention relates to a process for preparing murine interleukin 2 (hereinafter "IL-2") (formerly known in the literature as "T cell growth factor" or "TCGF"), and more particularly to a process for producing IL-2 in the presence of interleukin 1 (hereinafter "IL-1") (formerly known in the literature as "lymphocyte-activating factor" or "LAF") from murine malignant cells which are incapable of producing IL-2 by mitogen stimulation alone.

Background Art

Various types of protein mediators (lymphokines) are produced when T lymphocytes undergo blast transformation from stimulation by, for instance, antigens, antibodies against surface components of the lymphocyte or certain plant mitogens. Two such lymphokines, IL-1 and IL-2, are known to modulate T and B cell immune responses in mammals, including: (1) enhancement of thymocyte mitogenesis; (2) induction of alloantigen specific cytotoxic T cell reactivity; and (3) assistance in the generation of helper T cells in antibody responses following stimulation with heterologous erythrocytes. In addition, IL-2 is capable both of sustaining the in vitro exponential proliferation of effector T cell lines and of inducing in vitro and in vivo generation of cytotoxic T cells from nude mouse spleens.

In the past, murine IL-2 has been produced by culturing normal rat and mouse spleen cells in tissue culture medium and stimulating the cells with a mitogen, such as phytohemagglutinin (hereafter "PHA") or concanavalin A (hereafter "Con A"). However, producing murine IL-2 by mitogen stimulation of normal spleen cells results in weak concentrations of IL-2. Very large volumes of IL-2 containing conditioned medium must be fractionated to produce only small quantities of purified murine IL-2. As a consequence, sufficient quantities of concentrated murine IL-2 have not been available for in vivo experimentation nor for effective study of the molecular characterization of this immunoregulatory molecule.

Gillis et al. have recently documented a process for producing murine IL-2 from malignant neoplastic cells by stimulation of the cells with a T cell mitogen. "Biochemical and Biological Characterization of Lymphocyte Regulatory Molecules-III. The Isolation and Phenotypic Characterization of Interleukin 2 Producing T Cell Lymphomas", 125 *The Journal of Immunology* 2570 (1980). A particular murine splenic lymphoma cell line from the B10.BR mouse, designated as LBRM-33, was found to produce several hundred times more IL-2 per milliliter than previously generated by mitogen stimulation of identical numbers of normal rat or mouse splenocytes.

Gillis et al., supra, also reported producing IL-2 from cloned LBRM-33 cells by culturing the cloned cells in tissue culture medium and stimulating the cells with a plant mitogen. Several of the cloned cell lines were found to produce high concentrations of IL-2 upon mitogen stimulation, while other cloned cell lines were found to be incapable of producing IL-2 in response to mitogen stimulation. Accordingly, a principal object of the present invention is to produce murine IL-2 from malignant cell lines which are incapable of producing IL-2 by mitogen stimulation alone.

DISCLOSURE OF THE INVENTION

The present invention relates to a process for preparing IL-2 from cloned malignant murine cells. The process includes culturing cloned malignant neoplastic cells, such as murine leukemia or lymphoma cells, in vitro, in a protein containing medium supplemented with various additives. The culture is stimulated by adding both IL-1 and a T cell mitogen to the medium to thereby produce a supernate which contains IL-2. After a period of time, the supernate is collected and assayed for the presence of IL-2.

The above process has been used in conjunction with a particular cloned cell line, designated as LBRM-33-1A5, which was produced by subcloning a specific murine radiation-induced splenic lymphoma cell line, designated as LBRM-33, derived from the B10.BR mouse. The LBRM-33-1A5 cell is on deposit with the American Type Culture Collection under deposit number ATCC-CRL-8079. LBRM-33-1A5 cells will not produce IL-2 by mitogen stimulation alone. However, applicant has found that subjecting this nonproducing clonal isolate to both a plant mitogen and the monokine IL-1 results in the generation of IL-2 in quantities several hundred times greater than previously produced by lectin stimulation of identical numbers of normal rat or mouse splenocytes. Applicant has also established that the concentration of IL-1 used affects the quantity of IL-2 produced.

Applicant has further determined that IL-1 can influence the level of IL-2 produced from various types of malignant murine cells which are capable of producing high titers of IL-2 by stimulation with mitogen alone. For instance, adding IL-1 to LBRM-33-5A4 lymphoma cells (cloned from LBRM-33 parent cells) cultured in a one-tenth optimum concentration of an appropriate mitogen has been found to boost IL-2 production back up to the same production level attained when optimum concentrations of the mitogen alone are used. The LBRM-33-5A4 cell is on deposit with the American Type Culture Collection under deposit number ATCC-CRL-8080.

BEST MODE OF THE INVENTION

Outline of Process

In accordance with the present invention, murine malignant neoplastic cells in the form of cloned leukemia and lymphoma cells are cultured in vitro in a protein containing medium supplemented with various additives. A T cell mitogen, together with the macrophage product, IL-1, are added to the culture medium to stimulate the cloned malignant cells into producing a supernate which contains IL-2. After a period of time, the supernate is collected and assayed for the presence of IL-2.

As another aspect of the present invention, IL-1 is used as a co-stimulant together with a suboptimum concentration of a T cell mitogen to reduce the quantity of the mitogen required to produce IL-2 from malignant murine cells which are capable of generating IL-2 through stimulation by the T cell mitogen alone.

The process of the present invention has been described by Gillis et al. in "T Cell Lymphoma Model for the Analysis of Interleukin-1 Mediated T Cell Activation", *Proceedings of the National Academy of Sciences* (1981). The process has been applied to various clones of a radiation-induced splenic lymphoma cell line, designated as LBRM-33, derived from the B10.BR mouse. In one specific clonal cell line, labeled as LBRM-33-1A5, which is incapable of producing IL-2 by mitogen stimulation alone, use of the present procedure has resulted in the production of several hundred times the concentration of IL-2 than previously has been generated by mitogen stimulation of identical numbers of normal rat or mouse splenocytes.

Applicant has previously established that the initial cell density of a particular malignant cell line, whether a parent cell line or a clone thereof, used in IL-2 production influences the amount of IL-2 produced per number of initial cells. Applicant has found that for LBRM-33 cells, or clones thereof, the initial density of the murine cells should preferably be in the range of about $6 \times 10^5$ cells per milliliter to $3 \times 10^6$ cells per milliliter, with an ideal concentration of approximately $1 \times 10^6$ cells per milliliter.

Murine malignant cell lines, and specifically the LBRM-33 lymphoma cells and clones thereof, may be grown in various types of appropriate cell culturing media which have been previously found to foster growth of T-cells. These culture media include Roswell Park Memorial Institute (hereafter "RPMI") medium, Click's medium and Dulbecco Modified Eagle Medium (hereafter "DMEM"). These culture media may be supplemented with various individual additives or combinations of additives, including fetal calf serum (hereafter "FCS") which has been heat-inactivated by, for example, applying heat at 56° C. for 30 minutes. The volume of FCS added may be equal from 2 to 10% of the total culture volume. Other additives include penicillin in a concentration range of approximately 20 to 250 units per milliliter, and preferably approximately 50 units per milliliter, and streptomycin in a preferred concentration range of from 20 to 250 micrograms per milliliter, and ideally approximately 50 micrograms per milliliter. These antibiotics are utilized to minimize the possibilities that unwanted foreign bacteria may contaminate the cultures. Further additives include: (i) fresh L-glutamine in a preferred concentration range of approximately 100 to 1000 micrograms per milliliter, with an ideal concentration of approximately 300 micrograms per milliliter; (ii) N-2 hydroxy-piperazine-XI$^1$-2-ethenesulfonic acid (hereafter "HEPES") buffer in a preferred concentration of from 10 to 60 mM, and ideally approximately 25 mM; and (iii) 2-mercaptoethanol in a preferred amount of $1 \times 10^{-5}$ to $5 \times 10^{-5}$ molar and ideally approximately $2.5 \times 10^{-5}$ molar NaHCO$_3$ in a concentration range of 5 to 25 millimolar and ideally about 16 millimolar also may be added to the culture media.

In the IL-2 production process of the present invention, several different stimulating mitogens may be utilized. These mitogens include different plant proteins, such as Con A, PHA, and pokeweed mitogen (hereafter "PKM"). With respect to malignant murine cell lines, or clones thereof, which are capable of producing IL-2 by mitogen stimulation alone, applicant has found that the particular concentration of mitogen added to the cell culture affects the concentration of IL-2 produced. For instance, as shown in Table 1 below, when a cell concentration of $1 \times 10^6$ LBRM-33-5A4 cells per milliliter are cultured in RPMI 1640 medium supplemented with 2% by volume FCS, if a concentration of 0.1% by volume PHA is used as a stimulant, IL-2 in a concentration of approximately 35.0 units per milliliter is produced. If the PHA concentration is increased to approximately 1.0% by volume, a maximum quantity of about 565 units per milliliter of IL-2 is generated.

TABLE 1

EFFECT OF IL-1 AND T CELL MITOGEN CONCENTRATION ON LBRM-33-5A4 and 1A5 CELL LINE IL-2 PRODUCTION

| Culture* | U/ml IL-2 Present in 24 hr. Supernate |
|---|---|
| 5A4 + 1% PHA | 565.0 |
| 5A4 + 0.1% PHA | 35.0 |
| 5A4 + IL-1+ | 0.0 |
| 5A4 + IL-1 + 1.0% PHA | 604.0 |
| 5A4 + IL-1 + 0.1% PHA | 525.0 |
| 1A5 + 1% PHA | 0.0 |
| 1A5 + 0.1% PHA | 0.0 |
| 1A5 + IL-1 | 0.0 |
| 1A5 + IL-1 + 1% PHA | 476.0 |
| 1A5 + IL-1 + 0.1% PHA | 513.0 |

*$10^6$ cells/ml in RPMI 1640, 2% FCS.
+10 U/ml.

Applicant has furthermore found that IL-1 influences IL-2 production from cloned malignant cells even in instances in which the cloned cells are capable of generating IL-2 by the addition of a mitogen stimulant alone. Specifically, IL-1 has been found to have the capacity to restore IL-2 production to maximum levels when suboptimum concentrations of a mitogen stimulant are utilized. For example, as shown in Table 1, addition of IL-1 (10 u/ml) has no appreciable effect on IL-2 production by 1% volume PHA stimulated LBRM-33-5A4 cells which were cloned from LBRM-33 parent cells. However, similar addition of IL-1 to 0.1% by volume PHA stimulated LBRM-33-5A4 cells boosts IL-2 production from low (35 u/ml) levels to those observed when optimal amounts of mitogen (1% PHA by volume) are employed (525 u/ml). Similar results were achieved using other cell lines capable of IL-2 production by mitogen stimulation alone, such as LBRM-33-4A2 which also is a clonal product of LBRM-33 parent cell. The LBRM-33-4A2 cells are on deposit with the Salk Institute in LaJolla, California.

More importantly, applicant has discovered that for cloned malignant murine cell lines which do not produce IL-2 in response to stimulation with any concentration of mitogen, co-stimulation with IL-1 and mitogen trigger such cells to produce IL-2. In fact, maximum concentrations of IL-2 are produced even when normally unresponsive malignant T cells are stimulated with an appropriate plant mitogen, provided that IL-1 is used as a co-stimulant. For example, as shown in Table 1, when LBRM-33-1A5 cloned cells are cultured in 2% FCS supplemented RPMI-1640, stimulation with 1% or 0.1% (optimal and suboptimal respectively) by volume concentration of PHA, no IL-2 production is detectable in supernates harvested some 24 hours later. Addition of IL-1 (10 u/ml) to identical 1% PHA stimulated cultures resulted in generation of 476 units per milliliter of IL-2. If the concentration of PHA is reduced 10 fold to 0.1% by volume, a maximal level of IL-2 (about 513 units/milliliter) is still produced, provided stimulation cultures contained 10 u/ml IL-1.

Applicant has further established that the concentration of IL-1 utilized in the process of the present invention influences the level of IL-2 production from cloned malignant murine cell lines, but not until the concentration of IL-1 is lowered to levels well below the level required to induce murine thymocyte proliferation. As illustrated in FIG. 1, the ability of IL-1 to induce thymocyte proliferation does not begin to diminish until the concentration of IL-1 is reduced below approximately 25 units per milliliter, with a 50% reduction occurring at an IL-1 concentration of about 8 units per milliliter. However, the addition of this particular concentration of IL-1 to LBRM-33-1A5 cells ($1 \times 10^6$ cells stimulated with a 1% by volume concentration PHA) still results in peak levels of IL-2 production. In fact, IL-2 production does not start declining until the concentration of IL-1 is lowered to below 0.5 units per milliliter. Even at an IL-1 concentration of 0.2 units per milliliter, approximately 165 units per milliliter of IL-2 were produced which is still at least 100 times the level of IL-2 produced from identical numbers of mitogen stimulated normal murine spleen cells.

Applicant has in addition determined that the ability of IL-1 to stimulate IL-2 production in cloned malignant murine cell lines does not require the continuous presence of IL-1 in the culture medium. As set forth in Table 2 below, exposure of LBRM-33-1A5 cells to IL-1 at a concentration of 10 units per milliliter for four hours and then subsequent culturing of the cells in 10% by volume FCS supplemented RPMI 1640 in the presence of 1% by volume PHA and 10 units per milliliter of IL-1 resulted in production of 426 units per milliliter of IL-2 after twenty-four hours. However, even if IL-1 is not added to the subsequent culture medium, substantially the same level of IL-2 was produced. Specifically, as also indicated in Table 2, if the LBRM-33-1A5 clonal cell line is pretreated for four hours with a concentration of 10 units per milliliter of IL-1, and next the cell line is thoroughly washed and then placed in a culture medium stimulated by only PHA (1% concentration by volume), 410 units per milliliter of IL-2 are still produced. This production characteristic suggests that the interaction of IL-1 with LBRM-33-1A5 cells to convert them to a state of IL-2 production, was relatively rapid in nature.

TABLE 2

CONVERSION OF LBRM-33-1A5 CELLS TO
IL-2 PRODUCTION DOES NOT REQUIRE THE CONTINUAL
PRESENCE OF IL-1

| Cell Lines* | Pretreatment (4 hr.) | Subsequent 24 Hr. Culture | U/ml IL-2 Present In 24 Hr. Supernate |
|---|---|---|---|
| LBRM-33-1A5 | None | 1% PHA | 0.0 |
| LBRM-33-1A5 | None | 1% PHA + 10 U/ml IL-1 | 379.0 |
| LBRM-33-1A5 | 10 U/ml IL-1 | 1% PHA | 410.0 |
| LBRM-33-1A5 | 10 U/ml IL-1 | 1% PHA + 10 U/ml IL-1 | 426.0 |

*$10^6$ cells/ml in RPMI 1640, 10% FCS

The quantity of IL-2 produced by stimulating cloned malignant murine cells with a plant mitogen varies with time. For instance, when $10^6$ LBRM-33-1A5 cells are cultured in RPMI-1640 supplemented with FCS and stimulated with a 1% by volume concentration of PHA and IL-1, IL-2 activity was first found to begin at about five to seven hours after PHA and IL-1 co-stimulation. Initial IL-2 activity occurs within this five to seven hour time period even if FCS is not added to the culture medium. Whether or not FCS is used, peak levels of IL-2 are reached approximately sixteen to twenty-four hours after stimulation by PHA. In the subsequent twenty-four hour period, the quantity of IL-2 present diminishes only slightly. Thus, optimal culture duration for producing IL-2 with LBRM-33-1A5 cells in RPMI-1640 medium activated with 1% PHA and IL-1 is from approximately sixteen to forty-eight hours.

The above-described process for producing IL-2 from murine malignant cell lines, such as LBRM-33-1A5 lymphoma cells, may be carried out in various environmental conditions. Preferably, however, the LBRM-33-1A5 culture should be maintained at a temperature range of approximately 35° to 38° C. and in a humidified atmosphere of from approximately 5 to 10% carbon dioxide in air. Also, ideally, the pH of the culture medium should be kept in slightly alkaline condition, in the range of approximately pH 7.1 to 7.4.

The malignant cell lines may be seeded in different types of containers including flat-bottom microplate wells and in various sizes such as in 100-microliter aliquots. Tissue culture flasks, such as flasks No. 3013 or 3024 from Falcon Labware, Div. Becton, Dickinson and Co. also may be used.

Microassay of IL-2

The activity levels of IL-2 produced by the mitogen and IL-1 stimulation of various cloned malignant murine cell lines, to ascertain the affect of IL-1 on IL-2 production, may be tested by using the microassay procedure discussed by Gillis et al. in "T-Cell Growth Factor: Parameters of Production and a Quantitative Microassay for Activity", 120 *The Journal of Immunology* 2027 (1978). The assay monitors the IL-2 dependent cellular proliferation of a mouse cytotoxic T cell line (hereafter "CTLL"). Once it is determined that nonproducer clonal cell lines can be induced into IL-2 production by the addition of IL-1, the microassay technique is then employed to determine optimum culture conditions for IL-2 production, such as optimum initial cell concentrations of LBRM-33-1A5, mitogen doses, IL-1 concentrations and harvest times, as discussed above.

Briefly, the microassay procedure includes seeding approximately 3000 CTLL (as IL-2 dependent normal effector T cell lines) cells in 200 microliter volumes in a $\log_2$ dilution series of potential IL-2-containing samples. The mixture is cultured for twenty-four hours at 37° C. in a humidified atmosphere at 5% carbon dioxide in air. Thereafter, the cultures are pulsed for approximately four hours with 0.5 microcuries of tritiated thymidine ([$^3$H]Tdr: 20 Ci/mM specific activity) after which time the cultures are harvested onto glass fiber filter strips, for instance with the aid of a multiple automated sample harvester. [$^3$H]Tdr incorporation is then measured by liquid scintillation counting. By this procedure, only the CTLL cells cultured in the presence of IL-2 incorporate [$^3$H]Tdr in a dose-dependent manner. CTLL cells cultured in the absence of IL-2 incorporate only scintillant control levels of [$^3$H]Tdr and are more than 95% trypan-blue positive after twenty-four hours of IL-2 deprivation. Units of IL-2 activity are determined by probit analysis of [$^3$H]Tdr incorporation data. A 1 unit/ml standard has been defined as the amount of IL-2 activity present in forty-eight hour tissue culture medium conditioned by Con A (5 microgram/ml) stimulation of an initial concentration of $10^6$ cells per milliliter of normal rat spleen cells. An assay of 1 unit/ml standard routinely stimulated approximately 10,000 cpm of CTLL [$^3$H]Tdr incorporation at a dilution of 1:2.

Preparation of IL-1

The IL-1 as utilized in the manner stated above for, inter alia, inducing IL-2 production from clones of the parent LBRM-33 malignant murine cell line may be prepared by, for instance, stimulating a particular macrophage tumor cell line, designated as P388D$_1$ with phorbal myristate acetate (hereafter "PMA"). Prior to use, the resulting supernate is preferably concentrated and partially purified by various procedures, such as by differential ammonium sulfate precipitation, di-ethyl amino ethyl (hereafter "DEAE") cellulose ion exchange chromotography and then Sephacryl S-200 gel exclusion chromotography.

The IL-1 activity level in the supernate is determined by ascertaining its capacity to enhance thymocyte mitogenesis. Thymocyte proliferation was assayed in microplate cultures in the presence of a log$_2$ dilution series of IL-1. Replicate samples each containing approximately $1.5 \times 10^6$ thymus cells (taken from 4–6 week old C3H/HeJ or CBA/J mice) are seeded in 200 microliter cultures in RPMI medium (containing 10% by volume) FCS 1.0 micrograms per milliliter of PHA or 1% PHA by volume, and a log$_2$ dilution series of IL-1. Following 72 hours of culture, microplate wells are pulsed for four hours with 0.5 microcuries of [$^3$H]Tdr and then harvested onto glass fiber filter strips in an identical fashion as detailed above for completion of IL-2 microassays, Gillis et al., supra, 120 *The Journal of Immunology* 2022 (1978). [$^3$H]Tdr incorporation is determined by liquid scintillation counting. In the absence of exogenous IL-1, only meager PHA induced thymocyte proliferation has been observed (less than 500 cpm) whereas in the presence of 10 u/ml of IL-1, marked thymocyte proliferation has been observed as exemplified by over 10,000 cpm of [$^3$H]Tdr incorporation in IL-1 containing cultures. This result is consistent with those described by Mizel et al., "Characterization of Lymphocyte-Activating Factor (LAF) Produced By the Macrophage Cell Line P388D$_1$", 120 *The Journal of Immunology* 1492 (1978).

EXAMPLE 1

Cell line samples of a particular cloned murine leukemic T cell, LBRM-33-1A5, in a concentration of $1 \times 10^6$ cells per milliliter were cultured in 200 microliter flat-bottom microplate wells (3596; Costar, Inc., Data Packaging, Cambridge, Massachusetts), in RPMI-1640 medium. The medium was supplemented with 5% by volume, heat-inactivated (56° C. for thirty minutes) FCS, 50 units per milliliter of penicillin, $2.5 \times 10^{-5}$ M 2- mercaptoethanol, 50 micrograms per milliliter of streptomycin, and 300 micrograms per milliliter of fresh L-glutamine. The volume of each culture, including the cell line sample, medium and supplements totaled approximately 100 microliters. The microwell cultures were then stimulated by adding 100 microliters of 2% by volume PHA (PHA-M, Grand Island Biological Co., Grand Island, N.Y.) and by adding IL-1 in concentrations of from 0.1 to 100 units per milliliter. The cultures were all maintained at approximately 37° C. in a humidified atmosphere of 5% carbon dioxide in air.

After 24 hours, the supernate samples from the cultures were pooled and assayed for IL-2 activity using the microassay procedure as discussed above. The results of the assay are set forth in FIG. 1.

EXAMPLE 2

Cell line sample of particular cloned murine leukemic T cells, LBRM-33-1A5 and LBRM-33-5A4, in concentrations of $10^6$ per milliliter were cultured in 200 microliter flat-bottomed microplate wells (3596 Costar, Inc., Data Packaging, Cambridge, Massachusetts), in RPMI-1640 medium. The medium was supplemented with 5% by volume, heat-inactivated (56° C. for thirty minutes) FCS, 50 units per milliliter of penicillin, $2.5 \times 10^{-5}$ M 2 mercaptoethanol, 50 micrograms per milliliter of streptomycin, and 300 micrograms per milliliter of fresh L-glutamine. The volume of each culture, including cells, medium and supplements, totaled approximately 100 microliters. The microwell cultures were then stimulated by addition of 100 microliters of either 2% or 0.2% by volume PHA (Grand Island Biological Co., Grand Island, N.Y.) and by adding IL-1.

IL-1 used for costimulation was prepared from supernates harvested from phorbol ester stimulated P388D$_1$ macrophage tumor cells and was further concentrated by successive ammonium sulphate precipitation, DEAE cellulose ion exchange chromotography and Sephacryl S-200 (Pharmacia Fine Chemicals, Piscataway, N.J.) gel filtration chromotography as detailed in Mizel et al., supra.

Replicate cultures contained PHA mitogen and either IL-1 (10 units per milliliter) processed as detailed above, or IL-1 that has been additionally exposed to 1% by volume phenylglyoxal, an arginine site-specific modifying reagent which irreversibly destroys IL-1 biological activity. The phenylglyoxal was removed from IL-1 (after 6 hours of treatment at room temperature) by passage of the solution over a 10 centimeter column of Sephadex G-25 (Pharmacia Fine Chemicals, Piscataway, N.J.) gel exclusion resin. As shown in Table III below, addition of IL-1 to mitogen stimulated LBRM-33-5A4 and LBRM-33-1A5 cultures had profound effects on IL-2 production. Although supplementation of optimal PHA stimulated (1% by volume) LBRM-33-5A4 cultures with exogenous IL-1 had little effect on resultant supernate IL-2 titers, addition of IL-1 to suboptimal (0.1% by volume) PHA stimulated LBRM-33-5A4 cells, boosted IL-2 production to 399 units per milliliter. In comparison, LBRM-33-5A4 cells cultured for 24 hours with 0.1% PHA in the absence of IL-1 produced a tissue culture supernate which contained only 85 units per milliliter of IL-2. Pretreatment of IL-1 with 1% phenylglyoxal ablated its capacity to induce (together with 0.1% PHA) any significant LBRM-33-5A4 cell IL-2 production.

In the case of cloned LBRM-33-1A5 cells, as shown in Table III, 24 hour PHA stimulation (either 1% or 0.1% by volume) resulted in no significant IL-2 production. However, supplementation of PHA stimulated LBRM-33-1A5 cell cultures with 10 u/ml of IL-1 lead to IL-2 production of approximately 400 u/ml. As was observed in the LBRM-33-5A4 cultures, prior exposure of IL-1 to phenylglyoxal abated its capacity to induce (together with PHA) any significant LBRM-33-1A5 cell IL-2 production. In that a modification of IL-1 (which results in loss of its biological activity on thymocytes) also destroyed the monokine's capacity to augment LBRM-33-1A5/LBRM-33-5A4 cell IL-2 production, these results confirm the ability of IL-1 to influence malignant cell line IL-2 production.

TABLE III

| Cell Line | Stimulant | IL-1 (10 u/ml) | U/ml IL-2 Present in 24 hour Culture Supernates |
|---|---|---|---|
| LBRM-33-5A4 | 1% PHA | −[1] | 515 |
| LBRM-33-5A4 | 1% PHA | +[2] | 436 |
| LBRM-33-5A4 | 1% PHA | +PG[3] | 495 |
| LBRM-33-5A4 | 0.1% PHA | − | 85 |
| LBRM-33-5A4 | 0.1% PHA | + | 399 |
| LBRM-33-5A4 | 0.1% PHA | +PG | 25 |
| LBRM-33-1A5 | 1% PHA | − | <10 |
| LBRM-33-1A5 | 1% PHA | + | 416 |
| LBRM-33-1A5 | 1% PHA | +PG | <10 |
| LBRM-33-1A5 | 0.1% PHA | − | <10 |
| LBRM-33-1A5 | 0.1% PHA | + | 385 |
| LBRM-33-1A5 | 0.1% PHA | +PG | <10 |

[1](−) = Not present in culture.
[2](+) = Present in culture.
[3](+PG) = Phenylglyoxal treated IL-1 present in culture.

As will be apparent to those skilled in the art to which the present invention is addressed, murine IL-2 production may be carried out by using parent cell lines and cell lines cloned therefrom, culture media, culture media additives and mitogen stimulants other than those specifically disclosed above, without departing from the spirit or essential characteristics of the invention. The particular processes described above are therefore to be considered in all respects as illustrative and not restrictive, i.e. the scope of the present invention is set forth in the appended claims rather than being limited to the examples of the IL-2 producing processes as set forth in the foregoing description.

What is claimed is:

1. A process for the production of IL-2, comprising culturing malignant murine T cells from a cell line which is incapable of producing IL-2 by T-cell mitogen stimulation alone, is capable of producing IL-2 and requires IL-1 for IL-2 production, in a culture medium containing a T-cell mitogen and IL-1; and recovering the IL-2 from the culture medium.

2. The process of claim 1, wherein said malignant murine cells which are not capable of producing IL-2 by T-cell mitogen stimulation alone, are capable of producing IL-2 and require IL-1 for IL-2 production, are composed of T leukemic cells or T lymphoma cells.

3. The process of claim 2, wherein said malignant murine cells which are not capable of producing IL-2 by T-cell mitogen stimulation alone, are capable of producing IL-2 and require IL-1 for IL-2 production, are clones of said T leukemic cells or T lymphoma cells.

4. The process of claim 2, wherein said malignant murine cells which are not capable of producing IL-2 by T-cell mitogen stimulation alone, are capable of producing IL-2 and require IL-1 for IL-2 production, are LBRM-33-1A5 cells.

5. The process of claim 2, 3, or 4, wherein the initial T leukemic cell or T lymphoma cell concentration is in the range of about $6 \times 10^5$ to $3 \times 10^6$ cells per milliliter.

6. The process of claim 1, 2, 3, or 4, wherein the T cell mitogen in the culture medium is a compound selected from the group consisting of phytohemagglutinin, concanavalin A or pokeweed mitogen.

7. The process of claim 6, wherein the concentration of phytohemagglutinin mitogen is between 0.1 to 2.0% by volume.

8. The process of claim 6, wherein the concentration of concanavalin A mitogen is between 10 to 100 micrograms per milliliter.

9. The process of claim 6, wherein the culture medium further includes either Roswell Park Memorial Institute medium 1640, Click's medium or Dulbecco's medium.

10. The process of claim 9, wherein the culture medium further contains one or more compounds selected from the group consisting of penicillin, streptomycin, fresh glutamine, Hepes buffer, $NaHCO_3$, fetal calf serum and 2-mercaptoethanol.

11. The process of claim 6, comprising recovering the IL-2 from the culture medium after approximately sixteen to forty-eight hours of culturing.

12. The process of claim 3, wherein said clones of said T lymphoma cells are clones of LBRM-33 lymphoma murine T cells.

13. A malignant murine cell line which is incapable of producing IL-2 by T-cell mitogen stimulation alone but which produces IL-2 in the presence of both a T-cell mitogen and IL-1, having the identifying characteristics of ATCC CRL 8079.

* * * * *